(12) United States Patent
Simeone

(10) Patent No.: US 10,823,609 B2
(45) Date of Patent: *Nov. 3, 2020

(54) CLOTHING ITEM OR WEARABLE ACCESSORY FOR USE WITH A SYSTEM FOR COMPUTING EXPOSURE TO SOLAR RADIATION OF AN INDIVIDUAL

(71) Applicant: SIHEALTH PHOTONICS S.R.L., Leghorn (IT)

(72) Inventor: Emilio Simeone, Leghorn (IT)

(73) Assignee: SIHEALTH PHOTONICS S.R.L., Leghorn (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/460,393

(22) Filed: Jul. 2, 2019

(65) Prior Publication Data

US 2019/0323884 A1   Oct. 24, 2019

Related U.S. Application Data

(62) Division of application No. 16/082,347, filed as application No. PCT/IB2017/000213 on Mar. 6, 2017, now Pat. No. 10,365,155.

(30) Foreign Application Priority Data

Mar. 7, 2016   (IT) .................. 102016000023261

(51) Int. Cl.
*G01J 1/00*   (2006.01)
*G01J 1/42*   (2006.01)
(Continued)

(52) U.S. Cl.
CPC .............. *G01J 1/429* (2013.01); *A61B 5/441* (2013.01); *G01J 1/0219* (2013.01);
(Continued)

(58) Field of Classification Search
CPC ........ G01J 1/429; G01J 1/0242; G01J 1/0219; G01J 1/0266; G01J 2001/0357;
(Continued)

(56) References Cited

U.S. PATENT DOCUMENTS 7,661,200 B2 *   2/2010   Bonnet ................. A61B 5/1116
33/1 N
2013/0314699 A1 *   11/2013   Jungerman ........... G01J 1/0266
356/139.01

(Continued)

FOREIGN PATENT DOCUMENTS

DE   9116921 U1   11/1994

*Primary Examiner* — Kiho Kim
(74) *Attorney, Agent, or Firm* — McGlew and Tuttle, P.C.

(57) ABSTRACT

A clothing item or wearable accessory for use with a system for calculating the exposure to sun radiation received on the different parts of the body by a person, including a wearable device (1) that communicates with a telecommunication mobile device (2) and a remote computing unit (3) operatively connected to satellites (4) to receive georeferenced data related to solar irradiation over time and set to associate the solar irradiance data to the geographical position, the posture and the orientation of the person (P) or of parts of the person's body.

9 Claims, 3 Drawing Sheets

(51) Int. Cl.
*G01J 1/02* (2006.01)
*A61B 5/00* (2006.01)
*H04L 29/08* (2006.01)

(52) U.S. Cl.
CPC .......... *G01J 1/0242* (2013.01); *G01J 1/0266* (2013.01); *H04L 67/12* (2013.01); *G01J 2001/0257* (2013.01); *G01J 2001/4266* (2013.01); *G01J 2001/4276* (2013.01)

(58) Field of Classification Search
CPC ...... G01J 2001/4266; G01J 2001/4276; A61B 5/441; H04L 67/12
See application file for complete search history.

(56) References Cited

U.S. PATENT DOCUMENTS

| | | |
|---|---|---|
| 2015/0041663 A1 | 2/2015 | Oliver et al. |
| 2015/0177057 A1 | 6/2015 | Lian et al. |
| 2016/0109289 A1* | 4/2016 | Eom .................... G01J 1/0242 250/372 |

\* cited by examiner

CLOTHING ITEM OR WEARABLE ACCESSORY FOR USE WITH A SYSTEM FOR COMPUTING EXPOSURE TO SOLAR RADIATION OF AN INDIVIDUAL

CROSS REFERENCE TO RELATED APPLICATIONS

This application is a divisional under 37 CFR 1.53(b) of pending prior application Ser. No. 16/082,347 filed Sep. 5, 2018 and claims the benefit (35 U.S.C. § 120 and 365(c)) of International Application PCT/IB2017/000213 filed Mar. 6, 2017, which designated inter alia the United States and which claims the priority of Italian Patent Application IT102016000023261 filed Mar. 7, 2016, the entire contents of each application are incorporated herein by reference.

FIELD OF THE INVENTION

The present invention pertains to a detection system of the dose of solar radiation received by a person.

More specifically, the system comprises a wearable device, such as a swimsuit or a pair of sunglasses, equipped with sensors to identify the position, posture and orientation of the person with respect to the position of the sun and connected to devices capable of providing a real-time measurement of the actually received radiation in each part of the body, possibly including the eyes.

BACKGROUND OF THE INVENTION

At present, systems that combine a dosimeter and clothes that can be worn by a person are known.

By way of example, document WO2013034288 is known, which describes a wearable device associated with a geolocalization device and a portable device (smartphone) that uses UV sensors for the measurement of the solar exposure of the person.

However, the systems of the known type do not allow the association of a detection of solar exposure, measured in particular on the basis of a georeferenced location and the user's posture.

Therefore, what is needed is a measuring and control system of the solar exposure of a person, which is capable of carefully differentiating the exposure levels based on the position and the posture of the person.

SUMMARY OF THE INVENTION

The present invention wants to overcome the drawbacks of the already known solutions and propose a device allowing a controlled exposure to solar radiation in a differential way for the different parts of the body by taking into account the direct solar radiation, diffused from the sky and reflected by the ground.

These objects have been achieved by developing a device according to at least one of the appended claims.

A first advantage is that, by means of the device of the invention, the measurement of the incident solar radiation is calculated through processing of satellite images related to the state of the atmosphere and therefore without the use of wearable optical sensors.

A further advantage is that it is possible to measure the position of the single parts of a person's body with respect to the direction of the sun (according to the azimuth and in inclination with respect to the zenith), thus identifying the most exposed parts and performing a real time three-dimensional measurement of the solar radiation and the corresponding accumulated dose for each part of the body according to the posture and orientation relative to the direction of the sun.

The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
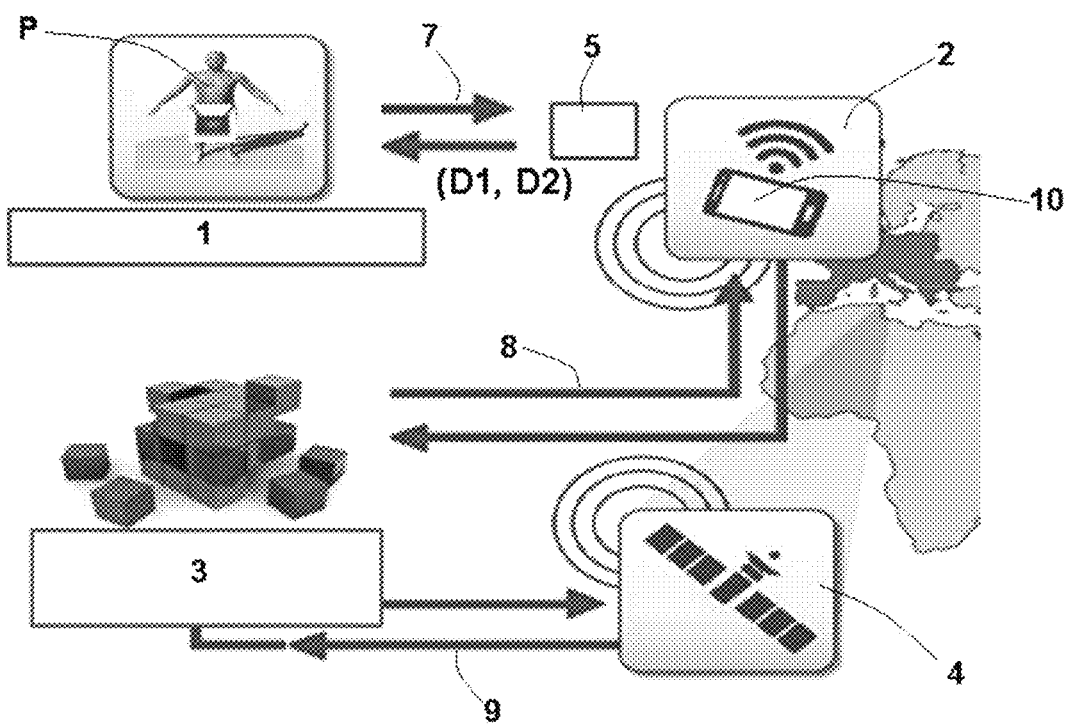
FIG. 1 is a schematic view showing a system according to the invention

With reference to the accompanying drawings, what is described is a system for the calculation of exposure to solar radiation received by a person, for a given range of wavelengths, which may be weighed according to a photobiological action spectrum of interest (e.g. CIE (Commission Internationale de l'Eclairage) erythema action spectrum in the range of 280 to 400 nm in case of UVs that may cause erythema, circadian action spectrum in the range of 380 to 580 nm, etc.).

In the shown example, the system essentially comprises a wearable device 1 with stable position and orientation with respect to the body of the person P, equipped with sensors 6 capable of detecting the attitude of the body at least according to the azimuth and in inclination according to the position of the body during sun exposure.

Preferably, the position sensors 6 are integrally positioned on an accessory or clothing item that can be worn so as to uniquely identify the orientation and inclination of the body, for example at the center of a swimsuit, integrally placed on sunglasses according to a given direction, or embedded in an adhesive label applicable to an identified part of the body.

In a possible embodiment of the invention, the position sensors comprise a magnetometer and an at least one vertical accelerometer and the device may further comprise a brightness sensor for detecting the person's position, indoor or outdoor, and a sweating/wetting sensor, preferably positioned in the external position in order to best detect the surrounding brightness and the external moisture condition of the person's body.

The system also includes a geolocalization sensor 5 associated to the person P and a remote computing unit 3 capable of exchanging data with satellite means 4, for example via a communication interface 9, so as to receive georeferenced data related to solar irradiation over time, and thus be able to associate the solar irradiance data to the geographic position, the posture and the orientation of the person (P) or of parts of the person's body over time, to provide the overall incident irradiance and the relative associated dose accumulated over time for one or more points of the body of the person (P). Global solar irradiance G(t) to the point of the body into consideration at the instant t is defined as the sum of the contributions of the solar radiation components diffused by the sky D(t), directly by the solar disk I(t) and reflected by the ground R(t) incident at that point.

The unit 3 is also connected via an interface 8, for example via a wireless network, to a portable telecommunications device 2 (for example a smartphone with integrated GPS 5) positioned close to the person P which in turn comprises an interface 7 (for example, a wireless interface with RF or infrared communication technology) with the wearable device 1 and the geolocalization sensor 5 to receive from these data D1 relating to the position and the orientation of the person and further comprises means 10 (for example, a display or an audible alarm) capable of providing the person P with information associated with data D2, processed by the computing unit 3 and relative to the person's exposure to solar radiation.

During operation, the device 1 is applied to the clothing item or accessory, so as to assume a stable position with respect not only to the contact, but also to the overall arrangement of the person's body. To increase the accuracy of the measurement of how the different points of the body are oriented in space, the device can be multiple, that is, it can be made of similar units applied to different clothing items in different parts of the body (e.g. one for panties and one for bras) or wearable accessories (e.g. one for panties and one for glasses) or various adhesive labels applicable to the identified points of the body.

The sensors 6 of the possibly multiple device are able to detect the alignment of a point of the body in space at least in terms of angle of inclination with respect to the normal inclination to the local horizontal plane (e.g. upright, lying, sitting positions and with the torso bent forward at a certain angle with respect to the vertical line) and in terms of orientation on the horizontal plane with respect to a certain azimuthal reference direction (e.g. angle with respect to the geographic North). In a more advanced version, the sensors 6 of the possibly multiple device can measure the absolute alignment of the body with respect to the direction normal to the local horizon plane and with respect to the Earth's magnetic field (corrected for the geographic North later on) on the three axes x-y-z and their variation over time.

By way of example, an unsuitable accessory for the application of the device 1 is a watch or a strap, because the rotation of the wrist, although integral with the watch, does not provide reliable directions relative to the orientation of the body.

Figure 2:
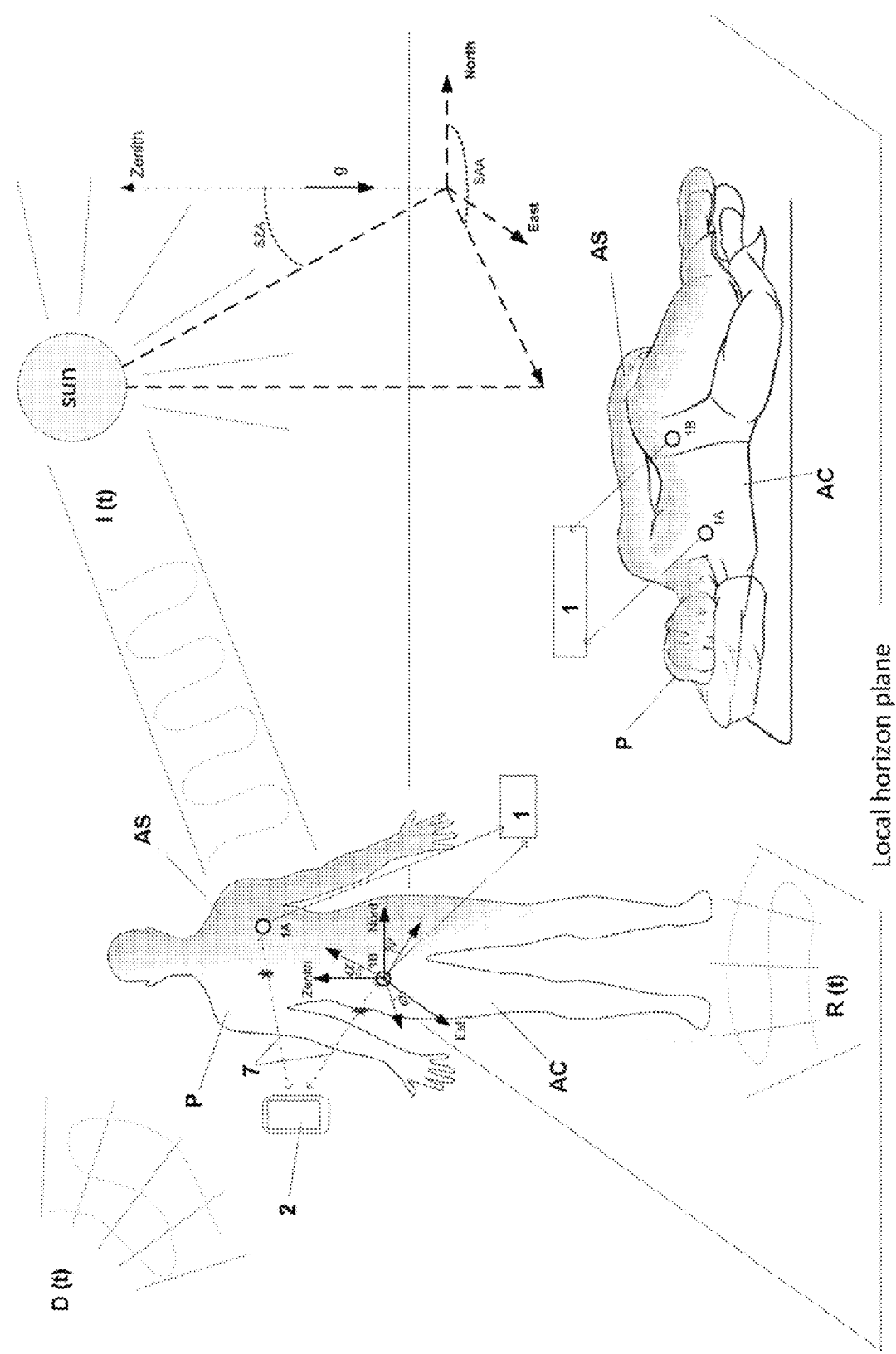
FIG. 2 is a view showing an example of use of the device for two different postures of the body.

Otherwise, a device positioned on a point of a swimsuit or a pair of sunglasses worn by the user makes it possible to understand how the body of the person is positioned, with particular reference to the position of the parts of the body having the greatest sensitivity, such as the shoulders or the face, by differentiating body areas AS that are the most exposed to solar radiation, and represented by way of example with darker shading in FIG. 2, and less exposed body areas AC, represented by way of example with light background.

In particular, in the case of device 1 integral to the lenses or to the frame of glasses, it is possible to detect at each instant t the different components of the incident solar radiation on the eyes of the person P for a given wavelength of interest, also possibly taking into account the optical characteristics of the lenses, by calculating interesting photobiological effects, such as the possible production of melatonin in the person P due to solar radiation, suitably weighted according to the circadian action spectrum in the range from 380 to 580 nm.

Once activated, for example thanks to an autonomous low-consumption power supply, the device 1 communicates with the device 2 (smartphone or tablet etc.) and sends the data concerning the position and orientation of the body.

At the same time, the geolocalization sensor, integrated or not, communicates the person's position to the device 2.

Through the interface 8, the portable telecommunications device 2 sends to the remote computing unit 3, for example a computing server, the data D1 of the person related to his/her geographical position, arrangement in space, and possibly relevant characteristics relating to sun exposure control (skin phototype, specific body morphology, diseases, sunscreens or therapeutic creams applied to different parts of the body, demographic information, optical characteristics of the glasses' lenses, etc.).

The unit 3 can thus process the data D1 in combination with satellite data D2 that associate the geographic location and the arrangement of the body in space, a specific global solar irradiance and the relative dose affecting one or more parts of the 3D-modeled body surface.

For example, the data D2 will provide different intensities of the direct, diffused and reflected component of solar radiation received in a given spectral range, depending on whether at that time the person P is in a cloudy or clear area, is on clear sand or at the sea and ha a given position (e.g. standing or lying) and orientation (facing East rather than West).

With this information, the unit 3 can calculate the quality and the quantity of solar radiation over time (global spectral irradiance possibly weighted with a photobiological spectrum of interest) of one or more points on the body, and send the person information relating to the dose received or still to be received for each point of the body (e.g. 3D dosimetric thematic map), through the communication means 10 (typically the smartphone display), for instance in order to:

1) suggest behaviours that allow the person not to exceed the preferred thresholds of exposure to solar radiation (e.g. alarm to stop the exposure;

2) make the solar radiation dose that has been received a homogeneous dose among the different parts of the body involved (e.g. by suggesting to change the position and orientation of the body);

3) information concerning the calculation of a desired exposure time of at least a portion of the person's body and/or the calculation of a recommended amount of sunscreen to be applied or even the recommended characteristics of sunglasses to be worn.

Specifically with reference to FIG. 2, the functioning of the system is described in an example of use of the device for two different postures of the body of a person P.

Through the remote computing system 3 (or even via a portable device 2 when provided with computing abilities and solar ephemerides) the two angles of the sun position on of the local horizon of the person P for the time t are obtained, as well as the three components of the solar radiation (diffused radiation D(t), direct radiation I(t) and reflected radiation R(t)) from satellite data processing, taking into account the local ground reflection coefficient for the considered wavelength as well.

The same remote computing system 3, preferably on the basis of a 3D model of the human body associated to the person P (for example MakeHuman—open source 3D model of the human body) and a finite element B(i,j,k) representation of its surface (possibly enriched with specific morphological data) is able to monitor the global solar irradiance over time G (t,B(i,j,k)) for each point of the body of the person P.

The orientation of each point B(i,j,k) is calculated according to the 3D model starting from the measurements obtained from the device 1 pertaining to the orientation data at the time t for one or more known points B(a,b,c) wherein the device has been positioned integrally to the body, depending on its position and orientation with respect to the cardinal axes.

The orientation of B(i,j,k) is defined as at least the azimuth, i.e. the angle formed by projection on the horizontal plane of the line normal to the surface in B(i,j,k) with the geographic North, and the inclination, i.e. the angle formed by the line normal to the surface in B(i,j,k) with respect to the line normal to the local horizontal plane.

The more numerous and spaced are the devices 1 applied onto the body in known points, the more accurate the orientation estimate of the other points B(i,j,k) of body surface area according to more complex 3D body models will be.

The calculated map G(t, B(i,j,k)) and the possible application of an action spectrum of photobiological interest is then made known to the person P via the terminal 2, by suggesting different types of behaviour based on the dose Dose(t, B(i,j,k)) obtained as an integral over time G and by also taking into account any photoprotective measures (e.g. suggestion of movements, rotations, total protection through clothing or accessories such as hats, glasses . . . ) and triggering of alarms should a safety threshold dose be reached (e g minimum dose that may cause erythema or other photobiological effects of interest) for any one of the points B(i,j,k) of the body surface area.

Figure 3:
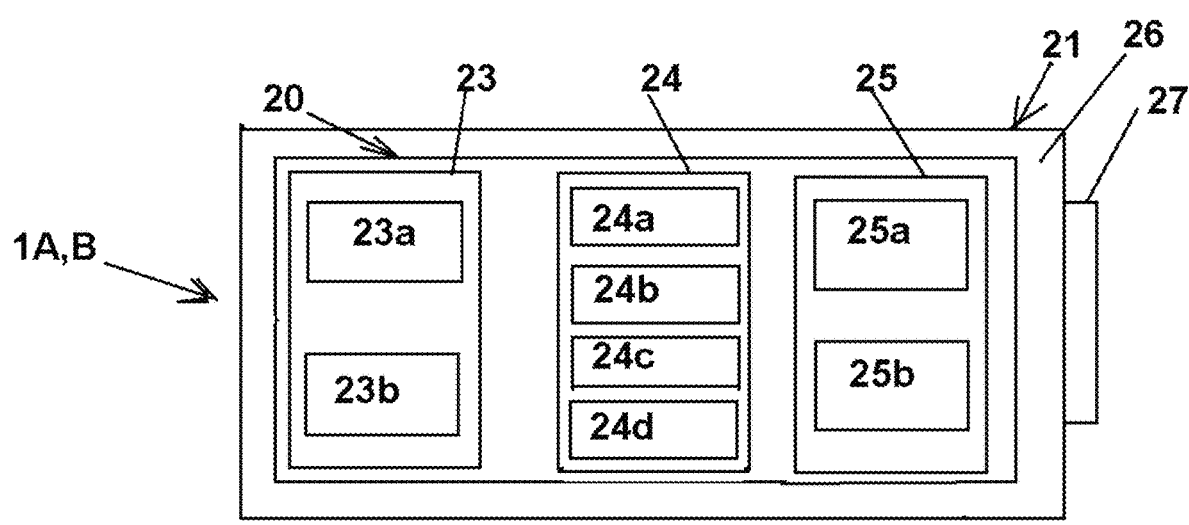
FIG. 3 is a schematic view showing a preferred composition of a device according to FIG. 2.

FIG. 3 shows in particular the application to the person P of an exemplary version of the embodiment of the device 1 previously shown in FIG. 1.

In this version, the device 1 is composed of two identical units 1A and 1B, each constituted by an electronic subsystem 20 and a fastening subsystem 21 (e.g. mechanical) to the person's body or an accessory integral therewith. The use of one or more units constituting the device 1 advantageously allows to detect the orientation and the position of the person with respect to the various components of solar radiation. The electronic subsystem 20 is composed for example by a detection module 23, an acquisition module 24 and a communication module 25, which are hereunder explained in detail.

The detection module 23 may comprise:
23*a*. A 3-axis accelerometer with an integrated 3-axis gyroscope (such as those that can be found integrated within the ST LSM6DS33 chip)
23*b*. A 3-axis magnetometer (such as those that can be found integrated within the ST LIS3MDL chip)

The different types of sensors can work together to generate data related to the angle and the angular movement of the device if compared to the axes of the magnetic field and the Earth's gravitational axis for each of the body parts: the upper portion (torso) and the lower portion (pelvis). Data can be generated with an adjustable frequency, typically between 200 Hz and 0.01 Hz.

The detection module 24 may comprise:
24*a*. A battery (e.g. a lithium polymer battery)
24*b*. A mass data storage support (for example, a NAND flash memory)
24*c*. A microcontroller (for example, one of the AtMega Atmel series)
24*d*. An electronic control system for the proper functioning of the system.

The acquisition module performs the following functions:
It manages the power supply to the various components of the device and battery recharge.
It allows data interfacing among components.
It handles data collection from sensors, and it may temporarily store them on an integrated data storage device.
It handles the communication with the device 2 (e.g. smartphone) by using the communication interface 7. Communication may be uninterrupted or upon request of the smart device.

The communication module 25 may comprise:
25*a*. A communication chip (such as a Bluetooth 4.0 LE module that can be integrated within the Nordic Semiconductor nRF51822 chip)
25*b*. A communication antenna, e.g. with Bluetooth technology.

The mechanical fastening subsystem 21 can be composed of two or more modules:
a containment module 26 of the electronic subsystem that is probably made of non-flexible plastic material, at least water and dust-proof (e.g. IP65-compatible)
one or more mechanical fastening modules 27 for integrally fastening the device to the human body which is being measured, which could be made of plastic material (flexible or rigid materials depending on the application) and which may be similar, for example, to a bracelet, a necklace, an anklet, a clip, a belt, or other wearable items that could be even adhesives which can be directly applied to the skin of the person in a certain position of the body.

In a typical operating form, the device 2 that presents the data to the person P allows the initialization of the measuring system at time t0, allowing it to interact with the person P to identify the mechanical positioning of the device 1 on the body and the position of the body at that instant. For example: unit 1A at the centre of the chest, unit 1B at the front central position at the pelvis level, position type: upright. For safety and calibration check reasons, it may also be possible to verify the correspondence of the calculations by asking the person P to verify their accuracy by orienting according to a known point based on which the sensor is mounted oriented towards the direction of the sun (if the sky is clear) or the geographical North (if the person P has another independent compass).

The invention has been described with reference to a preferred embodiment, but it is understood that equivalent modifications can then be made without departing from the scope of protection granted to the present industrial patent.

While specific embodiments of the invention have been shown and described in detail to illustrate the application of the principles of the invention, it will be understood that the invention may be embodied otherwise without departing from such principles.

What is claimed is:
1. A clothing item or wearable accessory having a stable position and orientation with respect to a body of a person, the clothing item or wearable accessory comprising:
a device provided with sensors capable of detecting a position of the body according to an azimuth and an inclination with respect to a vertical line depending on the position that the body has during sun exposure; and
a means for sending collected data concerning the position and an orientation of the person to a system used to calculate the exposure to solar radiation received by the person.

2. A clothing item or wearable accessory according to claim 1, further comprising:

brightness and sweating/wetting sensors.

3. A clothing item or wearable accessory according to claim 2, wherein the brightness and the sweating/wetting sensors are positioned on an outside of the device of the clothing item or wearable accessory.

4. A clothing item or wearable accessory according to claim 1, wherein the sensors capable of detecting a position of the body are integrally positioned on the clothing item or wearable accessory so as to uniquely identify the orientation and inclination of the body of the person.

5. A clothing item or wearable accessory according to claim 1, further comprising:

a plurality of clothing items or wearable accessories, wherein the position sensors are integrally positioned on the plurality of clothing items or wearable accessories, so as to identify the orientation and inclination of parts of the body of the person.

6. A clothing item or wearable accessory according to claim 1, wherein the position sensors comprise a magnetometer and at least one vertical accelerometer.

7. A clothing item or wearable accessory according to claim 1, wherein the means for sending collected data concerning the position and an orientation of the person comprises a wireless interface.

8. A clothing item or wearable accessory according to claim 1, wherein the clothing item is a swimsuit and the position sensors are integrally positioned at a center of the swimsuit.

9. A clothing item or wearable accessory according to claim 1, further comprising:

sunglasses, wherein the position sensors are integrally placed on the sunglasses.

\* \* \* \* \*